(12) United States Patent
Kreutz et al.

(10) Patent No.: US 6,352,529 B1
(45) Date of Patent: Mar. 5, 2002

(54) INTEGRATED LONG ABSORBENT ARTICLE HAVING STEPPED PANTY FASTENING ADHESIVE

(75) Inventors: Karen Ann Kreutz, Friedrichsdorf; Rachel Ann Lawton, Frankfurt, both of (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/554,487

(22) PCT Filed: Nov. 12, 1998

(86) PCT No.: PCT/US98/24174

§ 371 Date: May 15, 2000

§ 102(e) Date: May 15, 2000

(87) PCT Pub. No.: WO99/23987

PCT Pub. Date: May 20, 1999

(30) Foreign Application Priority Data

Nov. 12, 1997 (EP) .............................. 97119753
Jul. 3, 1998 (EP) .............................. 98112335

(51) Int. Cl.$^7$ ................................ A61F 13/15
(52) U.S. Cl. .................... 604/385.03; 604/385.01; 604/385.04
(58) Field of Search .............. 604/385.01, 385.03, 604/385.04, 386, 387

(56) References Cited

U.S. PATENT DOCUMENTS

| 3,570,491 A | * | 3/1971 | Sneider | 128/290 |
| 4,536,181 A | * | 8/1985 | Cook | 604/387 |
| 4,848,572 A | * | 7/1989 | Herrera | 206/440 |
| D392,736 S | * | 3/1998 | Erickson | 24/4 |
| 6,254,582 B1 | * | 7/2001 | O'Donnell et al. | 604/385.05 |

* cited by examiner

Primary Examiner—John G. Weiss
Assistant Examiner—Jacqueline F Stephens
(74) Attorney, Agent, or Firm—Ingrid N. Hickman; Kevin C. Johnson; Steven W. Miller

(57) ABSTRACT

The present invention relates to absorbent articles such as sanitary napkins, catamenials or adult incontinence inserts which are used in combination with undergarments. The absorbent articles according to the present invention have a minimum length of 255 mm, i.e., they are relatively long absorbent articles, and they are provided with a fastening adhesive to attach them to the undergarment during use. In particular, the present invention relates to such absorbent articles which are made from several layers which are joined to each other by integrating adhesive connections. The fastening adhesive is provided with an asymmetry in respect to the longitudinal direction and at least one of the integrating adhesive connections is at least co-extensive with fastening adhesive.

6 Claims, 4 Drawing Sheets

INTEGRATED LONG ABSORBENT ARTICLE HAVING STEPPED PANTY FASTENING ADHESIVE

FIELD OF THE INVENTION

The present invention relates to absorbent articles such as sanitary napkins, catamenials or adult incontinence inserts which are used in combination with undergarments. The absorbent articles according to the present invention have a minimum length of 255 mm, i.e. they are relatively long absorbent articles, and they are provided with a fastening adhesive to attach them to the undergarment during use. In particular the present invention relates to such absorbent articles which are made from several layers which are joined to each other by integrating adhesive connections. A fastening adhesive is provided with an asymmetry in respect to the longitudinal direction and at least one of the integrating adhesive connections is at least co-extensive with the fastening adhesive.

BACKGROUND OF THE INVENTION

Fastening adhesive for sanitary napkins are well-known in the art. Usually they cover part of the garment facing surface of sanitary napkins. The adhesive allows improved fixation of the napkins to the undergarment when applying the product and during use.

The dimensions of such panty fastening adhesives are influenced by several factors. One aspect is that they should cover as large an area as possible in order to provide firm attachment of the napkin to the undergarment. On the other hand the adhesive must not extend to areas which could possibly attach to the skin of the wearer since that would cause an unacceptable discomfort when using the product. Therefore, when considering the crotch portion of an undergarment typically products having been provided with an adhesive along the longitudinal length of the sanitary napkin such that the adhesive cannot extend beyond the smallest crotch width of the undergarment minus a certain safety margin to allow variation in placement of the napkin in the undergarment depending on user accuracy.

The other aspect when deciding on the panty fastening adhesive dimensions is how to provide the panty fastening adhesive onto the garment facing surface of a sanitary napkin in a mass production process. Many processes have been considered in this respect. EP-A-745 386 discloses printing of panty fastening adhesives in order to allow any shape of panty fastening adhesives to be provided. However, it is still most common to provide panty fastening adhesives by continuous coating or continuous spraying. The panty fastening adhesive is applied while the sanitary napkin moves on a band or belt in longitudinal direction. This automatically results in straight adhesive dimensions, which, when combined with an on-off switching of the adhesive application system, creates a rectangular stripe, or a series of rectangular stripes, on the garment facing surface of a sanitary napkin. By default these stripes cannot reach into a region of the sanitary napkin which extends beyond the smallest transverse dimension, i.e. width, of a sanitary napkin. In practical terms the adhesive needs to be even smaller in order to not extend to the peripheral edges of the sanitary napkin in the crotch region since this is also known to cause problems in comfort for the user, compare for example WO 92/04000. In U.S. Pat. No. 4,690,680 a rectangular adhesive design is suggested in which the adhesive is wider in the front and rear of the article and less wide in the center.

Hence it has become usual to provide sanitary napkins with a single or multitude of rectangular longitudinal stripes of panty fastening adhesive on their garment facing surface. This is acceptable for relatively short sanitary napkins of less than 255 mm, typically of less 240 mm. However, sanitary napkins extending along a larger length also are exposed to more variation in the forces they are exerted to (e.g. they extend from the crotch region beyond the public mons or beyond the anus into the buttocks region) and hence would benefit from better fixation to the undergarment, especially at the ends.

Another reason for not exceeding a maximum width in the crotch area of a panty fastening adhesive (even if a sanitary napkin would allow to provide an adhesive area wider than this certain width) is that the crotch width of undergarments is limited and hence providing adhesive beyond this crotch width is not useful but rather counter productive since it may expose adhesive to the skin of the wearer. This, however, is not the case outside the crotch region of the undergarment where the undergarment flares out into the front portion and into the rear portion covering the buttocks.

Based on the above an objective of the present invention is to provide long sanitary napkins, and in particular those which are asymmetrically shaped, i.e. having a longer and/or wider front or rear portion with a better attachment to the undergarment without violating the fundamental conditions of comfort (i.e. not extending beyond the crotch width of the undergarment with the adhesive) and manufacturing simplicity, for example by use of adhesive coating or spraying with no more variation than an on/off-switching mechanism.

The above has lead to the development of a panty fastening adhesive which is wider in one of the front or rear portion than in the center as disclosed in European application 97119753. This creates however another problem namely that the transmission of forces internally between the layers of the article needs to be sufficient to hold the whole article in place at least across the panty facing adhesive region. This is now achieved by the means of the present invention.

SUMMARY OF THE INVENTION

The present invention relates to absorbent articles such as a sanitary napkin for use in an undergarment having a garment facing surface and having a longitudinal centerline and a transverse centerline perpendicular to the longitudinal centerline which define a longitudinal direction and a transverse direction. The sanitary napkin comprises 3 regions, a first region in the center which has a length of at least 40 mm to cover the area on a wearer between the perineum and the most forward point of the labia majora during use. A second region extends in longitudinal direction on one side of the first region and a third region which extends on the opposite side of the first region. The second region is preferably longer than the third region such that the sanitary napkin is worn in an asymmetric fashion. The length in longitudinal direction of the sanitary napkin is at least 255 mm, preferably 270 mm and most preferably 300 mm or more.

The garment facing surface of the sanitary napkin comprises an adhesive for attachment of the sanitary napkin to an undergarment. The adhesive extends from the second region through the first region into the third region and has a width dimension in transverse direction at least in one point of the second region which is larger than the width in either the first or the third region. More particularly the adhesive in the first and third region is provided in a rectangular pattern relative to the centerlines and has a width in transverse direction between 35 and 60 mm while the adhesive in at least one point of the second region has a width in transverse direction of more than the width in the first and second region, preferably in the range 45 to 100 mm. In an even more preferable embodiment the adhesive in the second region is also rectangular relative to the centerlines.

The absorbent article comprises at least three components a generally liquid permeable topsheet, a generally liquid impermeable backsheet, and an absorbent core between the topsheet and the backsheet. Each of the components of the article has a garment facing surface and a wearer facing surface and at least one of the wearer facing surfaces of the components are joint at least partially by adhesive to the garment facing surface of an immediately adjacent component. This forms an integrating connection between the surfaces which integrating connection remains intact during usual use of the article. In particular according to the present invention at least one of the integrating connections is at least co-extensive with the panty fastening adhesive on the garment facing side of the article. In a preferred embodiment according to the present invention all components from the absorbent core layer to the backsheet are attached to each other with integrating connections which are all at least co-extensive with the fastening adhesive. In an even more preferred embodiment according to the present invention which will provide most controlled attachment of the article to the undergarment all component layers of the article are provided with integrating connections between the layers and all of these integrating connections are at least co-extensive with the panty fastening adhesive.

In another embodiment according to the present invention the absorbent article also comprises wings which are well-known in the art. The wings extend a length of at least 80% of the central first region of the sanitary napkin and preferably extend no more than 20% of the length of the third region into the third region while even more preferable the wings do not extend more than 50% of the length of the second region into the second region.

DETAILED DESCRIPTION OF THE INVENTION

Figure 1:
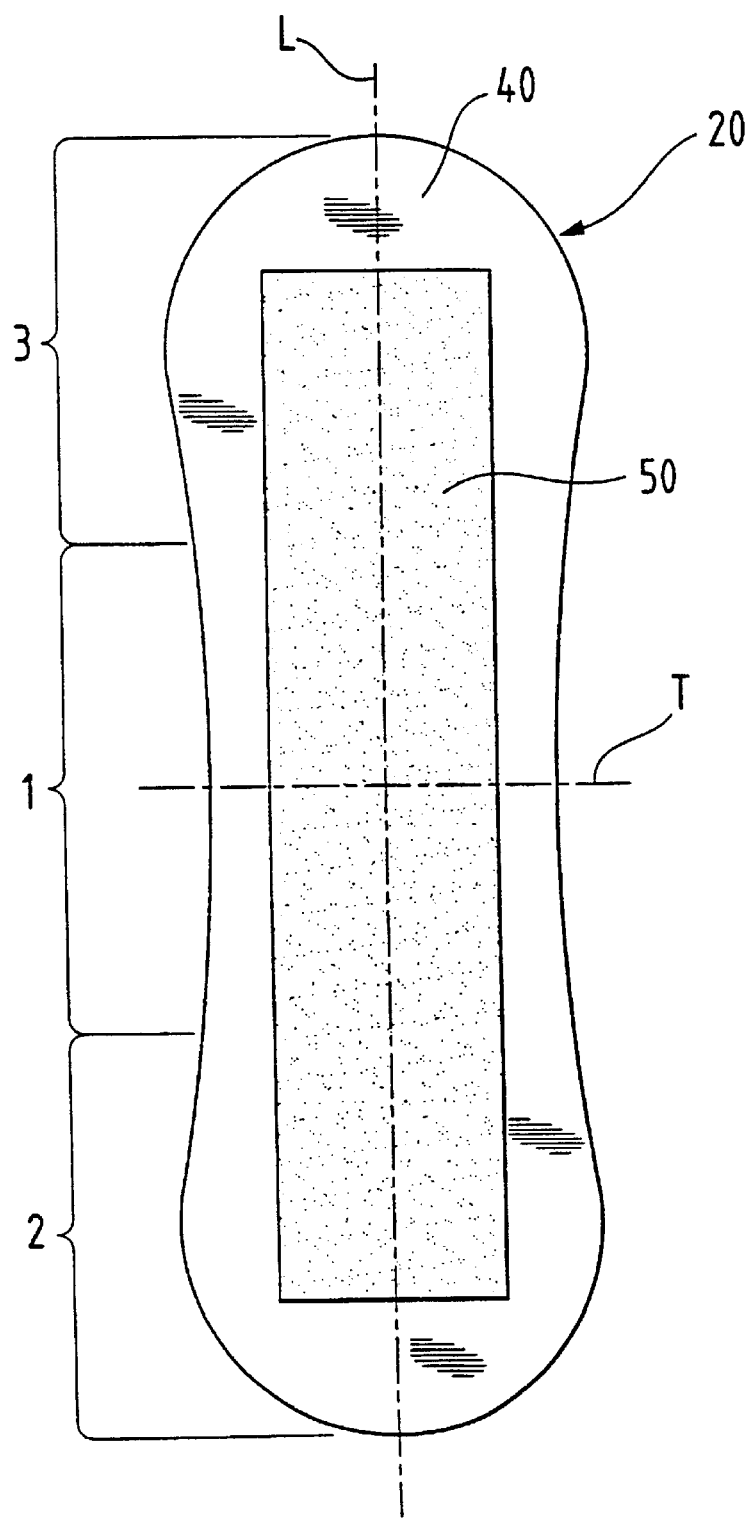
FIG. 1 shows a plan view of the garment facing surface of a sanitary napkin of the prior art.

According to the present invention an absorbent article for use in combination with an undergarment has an adhesive for attachment of the article to the undergarment. The design of the adhesive is particularly adjusted to the dimensions of the article and is asymmetric in longitudinal direction and in use reaches into a region in the undergarment distant from the crotch center. The layered components of the articles are attached to each other to integrate them during use.

In particular, sanitary napkins, catamenials and panty liners whether used for incontinence discharges or menstrual or other discharges are considered to be susceptible to the present invention. Typically such articles are of layered construction with each layer or group of layers and the article having a garment facing surface which is oriented to face in the direction of a garment during use of the article and a wearer facing surface facing in the opposite direction. Typically such articles comprise a liquid pervious topsheet forming the wearer facing surface of the article, an absorbent core and a breathable backsheet forming the garment facing surface of the article. The absorbent core is interposed between the topsheet and the backsheet.

Absorbent Article Components

The Topsheet

In general, the topsheet should have good liquid retention to maintain a dry surface and thereby keep the skin of the wearer dry; the absorbent core needs to provide enough absorbent capacity and the backsheet should prevent wet through (liquid permeability) to retain the absorbed fluid while preferably being breathable.

The topsheet is compliant, soft feeling, and non-irritating to the wearer's skin. The topsheet also can have elastic characteristics allowing it to be stretched in one or two directions in portions of the topsheet or throughout its extension. Further, the topsheet is fluid pervious permitting fluids (e.g., menses and/or urine) to readily penetrate through its thickness. A suitable topsheet can be manufactured from a wide range of materials such as woven and non woven materials; polymeric materials such as apertured formed thermoplastic films, apertured plastic films, and hydroformed thermoplastic films; and thermoplastic scrims. Suitable woven and non woven materials can be comprised of natural fibers (e.g., wood or cotton fibers), synthetic fibers (e.g., polymeric fibers such as polyester, polypropylene, or polyethylene fibers) or from a combination of natural and synthetic fibers or bi-/multi-component fibers.

Preferred topsheets for use in the present invention are typically selected from high loft nonwoven topsheets and apertured formed film topsheets. Apertured formed films are especially preferred for the topsheets because they are pervious to body exudates and yet non absorbent and have a reduced tendency to allow fluids to pass back through and rewet the wearers skin. Thus, the surface of the formed film that is in contact with the wearer remains dry, thereby reducing body soiling and creating a more comfortable feel for the wearer. Suitable formed films are described in U.S. Pat. Nos. 3,929,135; 4,324,246; 4,342,314; 4,463,045; and 5,006,394. Particularly preferred micro apertured formed film topsheets are disclosed in U.S. Pat. Nos. 4,609,518 and 4,629,643. A preferred topsheet for the present invention comprises the formed film described in one or more of the above patents and marketed on sanitary napkins by The Procter & Gamble Company of Cincinnati, Ohio as "DRI-WEAVE".

Topsheets having not a homogeneous distribution of liquid passage ways are also contemplated by the present invention such as for example only a portion of the topsheet comprising liquid passage ways or a film with apertures of various sizes. Typically such topsheets would have the liquid passage ways oriented such that they result in a centrally permeable and peripherally impermeable topsheet for liquids.

The wearer facing surface of the formed film topsheet can be hydrophilic so as to help liquid to transfer though the topsheet faster than if the body surface was not hydrophilic. In a preferred embodiment, surfactant is incorporated into the polymeric materials of the formed film topsheet such as is described in PCT-publication WO 93/09741. Alternatively, the wearer facing surface of the topsheet can be made hydrophilic by treating it with a surfactant such as is described in U.S. Pat. No. 4,950,254.

Another alternative are so called hybrid topsheets which incorporate fibrous and film like structures particularly useful embodiments of such hybrid topsheets are disclosed in PCT publications WO 93/09744; WO 93/11725 or WO 93/11726.

The topsheet typically extends across the whole of the absorbent structure and outside the area coextensive with the absorbent structure.

When referring to the topsheet a multi layer structure or a mono layer structure is contemplated. The hybrid topsheet mentioned above is such a multi layer design but other multi layer topsheets such as primary and secondary topsheet designs are also considered.

The Core

Positioned in fluid communication with, and typically underlying the topsheet is the absorbent core. The absorbent core provides fluid storage and distribution function and can also comprise multiple layers. The core can comprise any usual absorbent material or combinations thereof. It preferably comprises absorbent gelling materials usually referred to as "hydrogel", "superabsorbent", hydrocolloid" materials in combination with suitable carriers.

Suitable absorbent gelling materials for use herein will most often comprise a substantially water-insoluble, slightly cross-linked, partially neutralised, polymeric gelling material. This material forms a hydrogel upon contact with water. Such polymer materials can be prepared from polymerizable, unsaturated, acid-containing monomers, such as acrylic acid, which are well known in the art.

Suitable carriers include materials which are conventionally utilised in absorbent structures such as natural, modified or synthetic fibers, particularly modified or non-modified cellulose fibers, in the form of fluff and/or tissues. Suitable carriers can be used together with the absorbent gelling material, however, they can also be used alone or in combinations. Most preferred are tissue or tissue laminates in the context of this article.

An embodiment of the core, particularly useful in the application of the present invention, comprises a double layer tissue laminate which can be formed by folding the tissue onto itself. These layers can be joined to each other. Absorbent gelling material or other optional material can be comprised between the layers.

The absorbent core can include optional components normally present in absorbent webs such as odor control agents, in particular suitable zeolites or silicas.

The Backsheet

The backsheet primarily prevents the exudates absorbed and contained in the absorbent core from wetting articles that contact the absorbent product such as underpants, pants, pyjamas and undergarments. The backsheet is preferably impervious to liquids (e.g. menses and/or urine) and usually manufactured from a thin plastic film.

The backsheet typically extends across the whole of the absorbent core and can extend onto and form part of the topsheet by folding around the absorbent core. Thereby a topsheet configuration as disclosed in U.S. Pat. No. 4,342,314, column 16, lines 47–62 can be achieved without the requirement to selectively aperture the topsheet.

Preferably, the backsheet also provides breathability to the absorbent article by being at least water vapour permeable, preferably air permeable. The backsheet can be a laminate material e.g. of a combination of microporous film and/or non-woven material, and/or apertured formed film. Breathability if desired can be limited to the periphery or the center of the backsheet or it can be across the whole backsheet.

The Panty Fastening Adhesive

The sanitary napkin comprises an adhesive area on its garment facing surface which adhesive is protected by a cover means which cover means is released prior to use of the article. The adhesive area need not be fully covered by adhesive but may for example be provided by homogeniously distributed adhesive filaments leaving small areas uncovered between the filaments. Alternatively the "adhesive area" according to the present invention may be provided by sub portions of adhesive and is then defined as the area formed by the shortest possible line encircling all sub portions, however excluding those in the wings.

As can be seen in the prior art sanitary napkin (20) of FIG. 1 the garment facing side (40) which typically is provided by a liquid impermeable backsheet of such a sanitary napkin, comprises an adhesive (50). In general sanitary napkins have a longitudinal centerline (L) and a transverse centerline (T). In the prior art sanitary napkin of FIG. 1 the transverse centerline (T) is located in the middle of the sanitary napkin, i.e. it separates the sanitary napkin into two halves which are approximately of equal length in longitudinal direction. The shown sanitary napkin is also symmetrical in longitudinal direction to the transverse centerline (T). In contrast a sanitary napkin according to the present invention such as the sanitary napkins shown in FIGS. 2, 3 or 4 has a transverse centerline (T) which separates a napkin into two halves which are substantially not identical in length.

The transverse centerline (T) is located in a central or first region of a sanitary napkin. This first region has an extension in longitudinal direction sufficient and intended to cover the area on a wearer between the perineum and the most forward point of the labia majora. Based on medical studies this varies between about 40 mm and 80 mm on average women depending on sexual activity, child birth and other factors. Hence the minimum length of the first region is 40 mm but would preferably be at least 60 mm, more preferably at least 80 mm and most preferably at least 112 mm. The transverse centerline separates the first region into two halves in longitudinal direction which are substantially of equal length. This is obviously the case for conventional sanitary napkins of the prior art or for sanitary napkins of the present invention.

Sanitary napkins having a first region (1) according to the above definition also have a second (2) and a third (3) region outside the first region which are extending from the first region (1) to the longitudinal ends of the sanitary napkin. As can be seen from the FIGS. 2, 3 and 4 sanitary napkins according to the present invention have a second region (2) which is longer than the third region (3).

A panty fastening adhesive (50) in prior art sanitary napkins which are longitudinally symmetrical as shown in FIG. 1 will naturally extend an equal distance from said first region (1) into said second (2) and said third region (3). In contrast sanitary napkins according to the present invention have an undergarment adhesive attachment (50) which preferably extends in longitudinal direction further from the first region (1) into the second region (2) then it extends from the first region into the third region (3), as shown in the FIGS. 2, 3 and 4.

Figure 2:
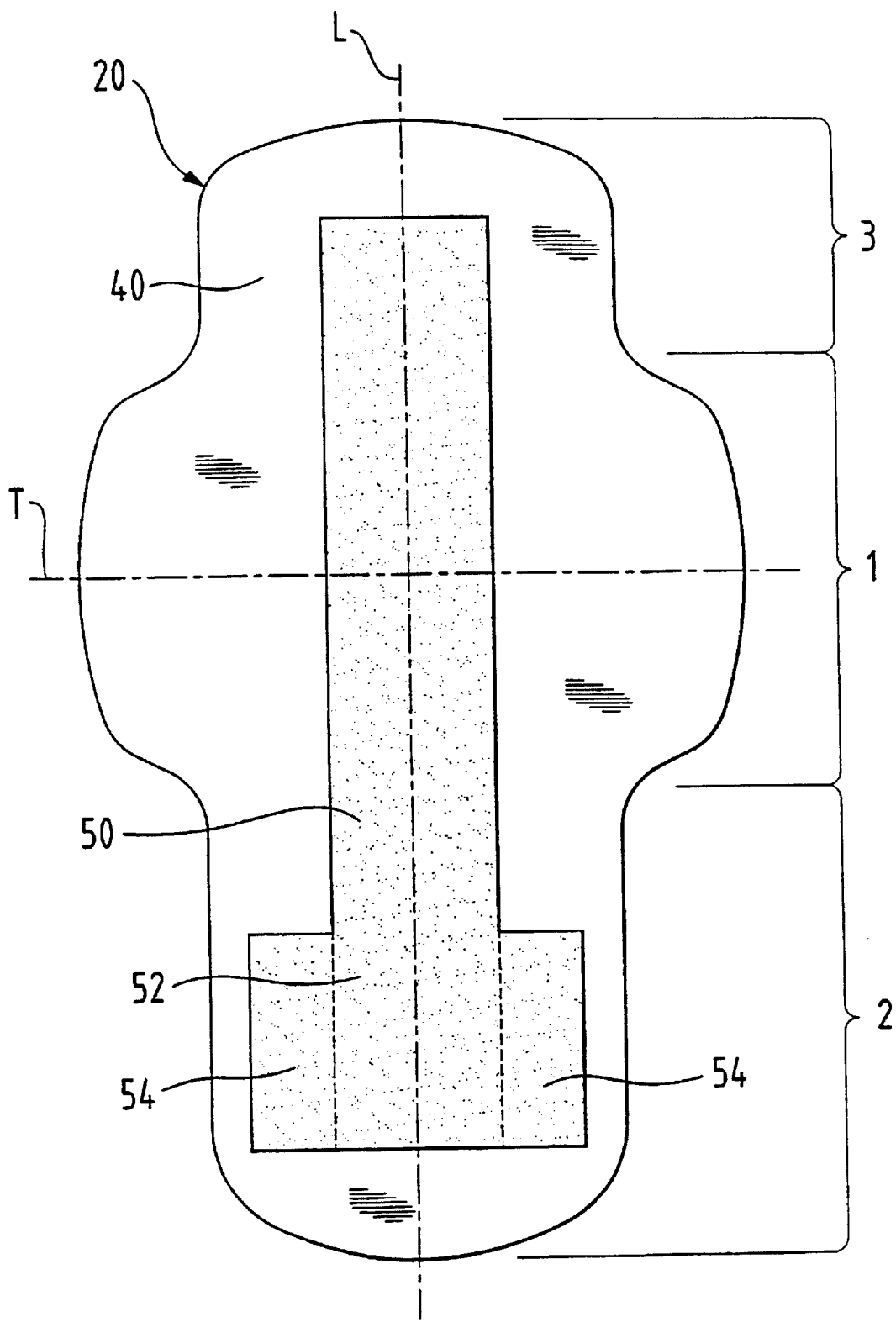
FIG. 2 shows a preferred embodiment of a sanitary napkin according to the present invention with a fastening adhesive on the garment facing surface of the napkin.
Figure 3:
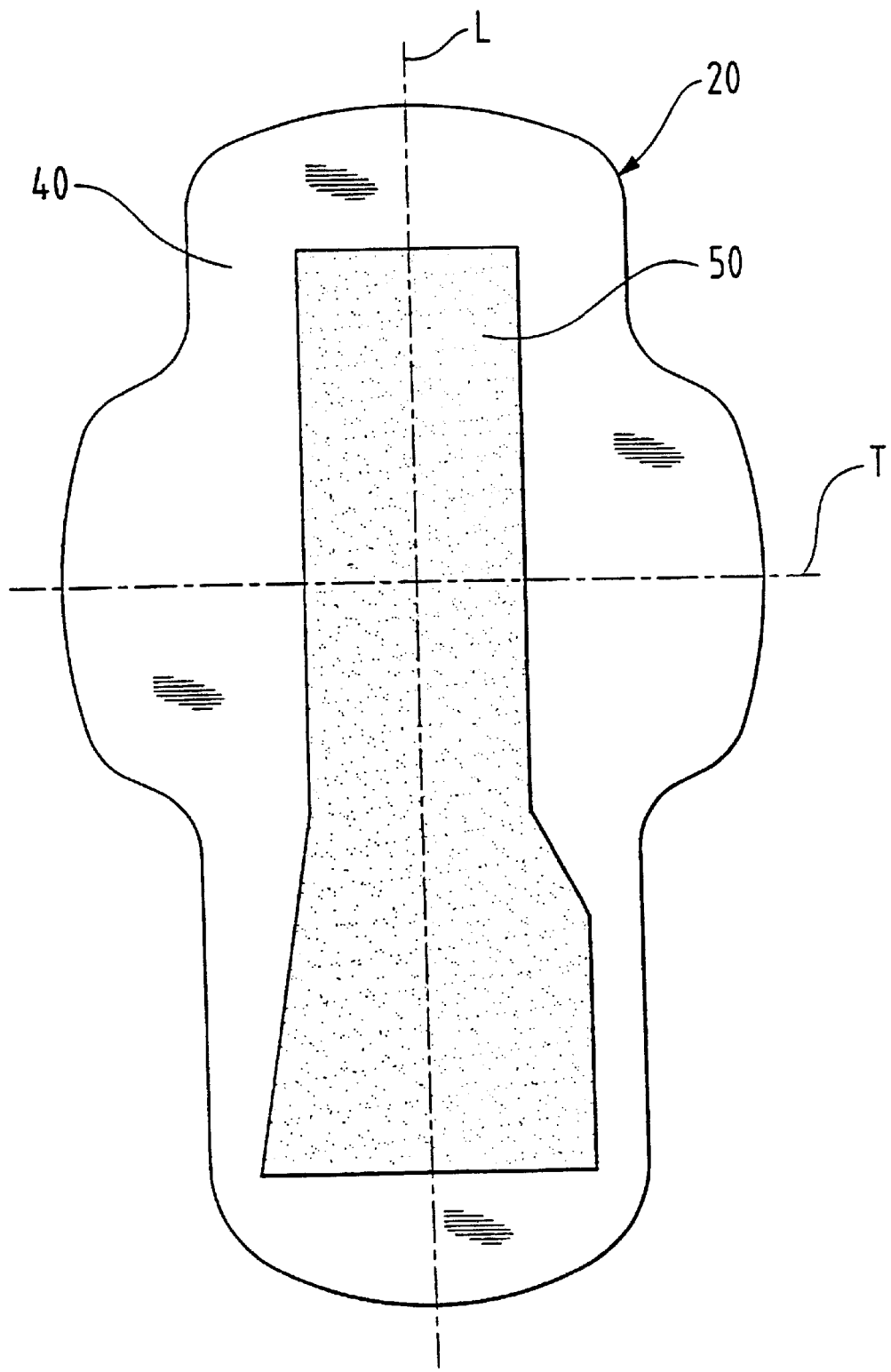
FIG. 3 shows an alternative embodiment of the present invention with a fastening adhesive on the garment facing surface with different dimensions on one side of the longitudinal centerline as a first alternative and on the other side of the longitudinal centerline as a second alternative.
Figure 4:
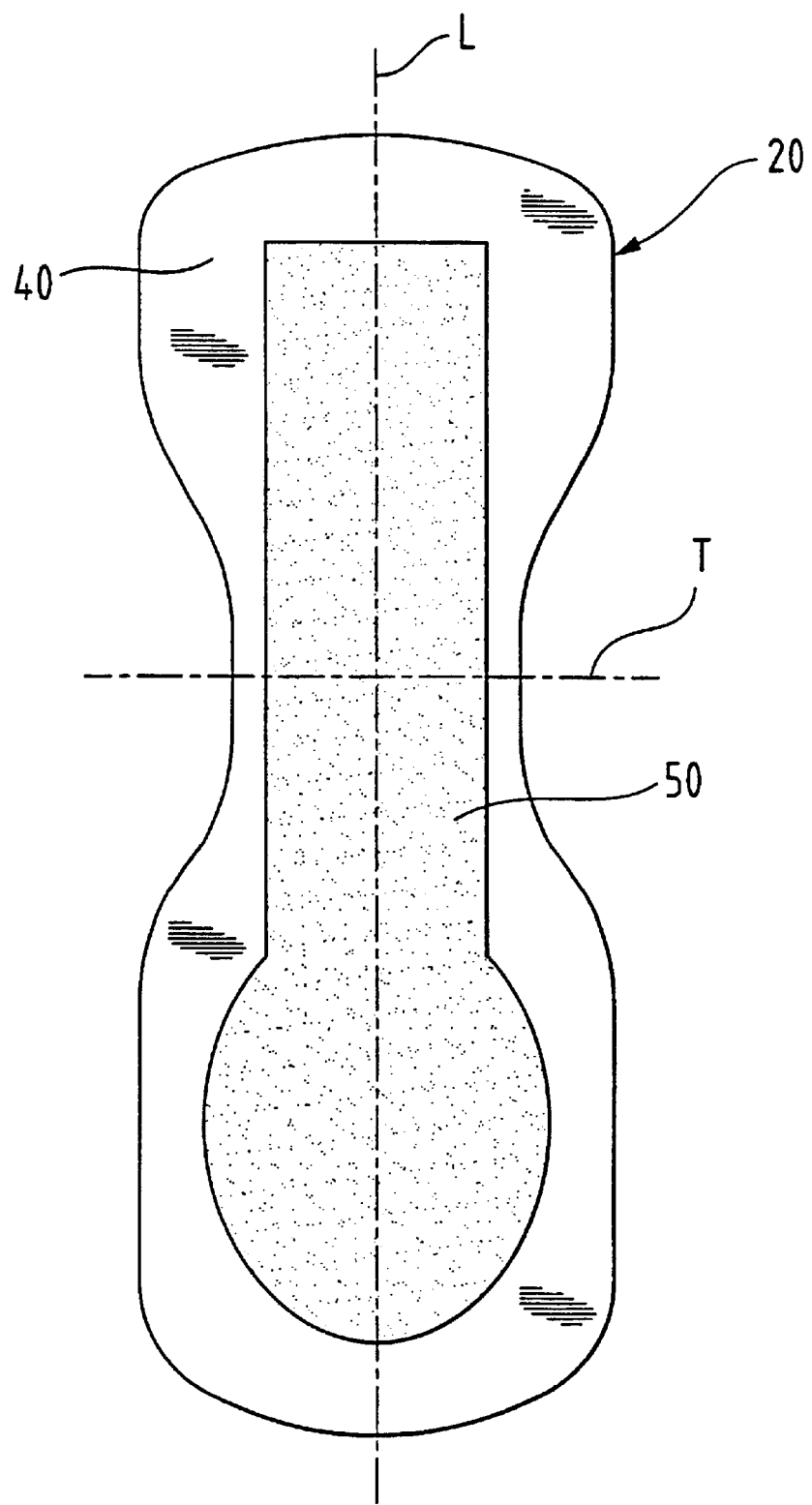
FIG. 4 shows another alternative embodiment according to the present invention.

According to the present invention the width in transverse direction of the adhesive in the second region (2) is wider in at least one point than the width of the adhesive in the first (1) and in the third region (3). FIG. 2 shows a particularly preferred shape of adhesive in which the adhesive is provided in a rectangular pattern, which is easy to provide when continuously manufacturing sanitary napkins in longitudinal direction. Two alternative shapes satisfying the width requirement according to the present invention are shown in FIG. 3 on the right and left side of the longitudinal axis. Both of the designs of the adhesive (50) shown in FIG. 3 also comprise non-rectangular portions. Another preferred embodiment is shown in FIG. 4 in which the wider portion of the adhesive (50) in the second region (2) is provided in a semi-oval shape.

It is also possible that the adhesive (50) in the wider portion of the adhesive in the second region (2) of sanitary napkins according to the present invention may comprise a different quantity of adhesive than the adhesive in the first or second region. For example the pattern shown in FIG. 2 can be provided by coating an adhesive in longitudinal direction through three coating means (e.g. slot coaters or spray nozzles). One coating means providing a central rectangular area (54) extending from the third (3) through the first (1) to the second (2) region (indicated by dashes in the second region (2)) and being similar to the adhesive shown in FIG. 1 for prior art sanitary napkins. In addition the areas of adhesive (54) extending beyond the rectangular portion (52) in the second region (2) of the sanitary napkin are provided by two additional coating means which may provide the same amount of adhesive per area or may provide a different amount of adhesive per area than the central coating means. In principle it would also be possible to provide different adhesives through the different coating means. In this context also stripes of adhesive instead of a completely coated surface could be provided. Then the adhesive area shown in FIG. 2 is the area inside the shortest possible line encircling all sup portions, excluding adhesive on the wings (not shown in FIG. 2). The same applies to FIGS. 3 and 4.

In an alternative way of providing the adhesive to the garment facing surface (40) of a sanitary napkin according to the present invention it would also be possible to provide the whole area in which the adhesive is wider in the second region (2) by a separate coating means while the adhesive in the first and third region of the sanitary napkin is provided by conventional adhesive coating means such as those used for prior art sanitary napkins according to FIG. 1.

As noted above sanitary napkins according to the present invention are preferably provided with flaps or wings extending beyond the undergarment crotch width and being folded around the undergarment crotch so as protect the undergarment side edges. Sanitary napkins with wings are shown in the preferred embodiments of FIGS. 2 and 3 while wings are not mandatory but only preferred in the context of the present invention since they provide additional fixation of sanitary napkins, particularly very long sanitary napkins.

Preferably as indicated in the background discussion above the width of the adhesive in the first region is such that it extends close to the side edges of the napkin as shown in FIG. 4.

The adhesive for fastening the article in an undergarment can be any adhesive useful for the desired application. Usually it is a pressure sensitive adhesive which can be applied in any way usual in the art. In particularly, the adhesive application can be by use of contact application means, such as printing or scraping or slot coating, or by non contact application, such as curtain coating, spraying or spiraling. The adhesive can be coated as hot melt or from a cold solution, either to the garment facing surface of the article or to the cover means which then carries it to the article.

The adhesive needs to be adapted to the desired application, e.g. it needs to support breathability if it is used in a breathable sanitary napkin. The adhesion force of the adhesive to the undergarment facing surface of the article needs to be larger or equal to that adhesion force which it has to the cover means. Also it is desirable to have an adhesive which does not separate during use from the article and leaves adhesive traces in the undergarment when separating the article from the undergarment.

Joining the Components of the Article Together

According to the present invention the absorbent article components are joined to each other in an integrating fashion. The objective being to ensure that the forces in a direction perpendicular to the layered components can be transmitted between the layers of the components such that all components of the article are held to the undergarment in a controlled fashion through the improved panty fastening adhesive disposition.

In order to achieve this the wearer facing surface and the garment facing surface of the layers of the components are joined to each other by an adhesive connection. The adhesive can be any which is usual in the art and its application can also be any conventional application. The preferred applications are the same as mentioned above for the panty fastening adhesive. This adhesive connection does not have to extend across the whole surface area of the article but in order to provide its integrating function needs to extend at least throughout the same area as the panty fastening adhesive. Hence an integrating connection between layers is achieved when providing an adhesive connection between layers of the components of the article which connection is co-extensive with or extending beyond the panty fastening adhesive.

The benefit of this integrating connection is already achieved when providing at least some of the layers of the components of the article with such integrating connections. However it is most preferable that the components providing the majority of the structural stiffness or stability of the article are integrated with the panty fastening adhesive through integrating adhesive connections. Usually the structural stiffness or stability of the article is primarily provided by the absorbent core component of the article and hence it is preferred that all layers between the backsheet and the absorbent core are integrated in an area co-extensive with or extending beyond the panty fastening adhesive. Even more preferred would of course be a design in which all layers of the article are provided with an adhesive connection which integrates them in an area at least co-extensive with the panty fastening adhesive.

An additional benefit other than control of the components of the article in respect to the undergarment during use is the handling of the absorbent article when manipulating it from the condition in which it is provided to the wearer into the condition in which it is used. In other words article without the integrating connections according to the present invention have a higher probability of being improperly handled such as for example crumpled or deformed already upon placement in the undergarment.

It will be appreciated by those skilled in the art that the above explanations and embodiments are disclosed for the purpose of illustration and enablement but that the present invention is defined by the limits given in the claims.

What is claimed is:

1. A disposable absorbent article (20) for use in an undergarment comprising at least three components
   a generally liquid permeable topsheet
   a generally liquid impermeable backsheet joined to said topsheet
   an absorbent core between said topsheet and said backsheet, said article and each of said components having a garment facing surface and a wearer facing surface, said article (20) having a longitudinal centerline (L) and a transverse centerline (T) perpendicular to said longitudinal centerline (L), said article (20) comprising three regions (1,2,3) along said longitudinal centerline (L),
      a first region (1) which includes said transverse centerline (T) and which has a length of at least 40 mm to cover in use the area on a wearer along said longitudinal direction between the perineum and the most forward point of the labia majora,
      a second region (2) which extends along said longitudinal direction on a first side of said first region (1), and
      a third region (3) which extends along said longitudinal direction on a second side opposite said first side of said first region,
      said second region (2) being longer than said third region (3), said article (20) having a length of at least 270 mm, in longitudinal direction, said garment facing side (40) of said article (20) comprising a fastening adhesive (50) for attachment to said undergarment, said article (20) being characterized in that said fastening adhesive (50) extends from said second region (2) through said first region (1) into said third region (3) and in that the fastening adhesive (50) width in transverse direction at least at one point of said second region (2) is larger than the fastening adhesive (50) width in transverse direction at one point of said first region (1) and of said third region (3).

2. An article (20) according to claim 1 characterized in that all components of said article from and including said absorbent core to said backsheet are provided with integrating connections and that all these integrating connections are at least coextensive with said fastening adhesive (50).

3. An article (20) according to claim 1 characterized in that said fastening adhesive (50) in said first region (1) and third region (3) is provided in a rectangular pattern relative to said centerlines (L, T) and has a width in transverse direction in the range of 35 mm to 60 mm in said first region (1) and said third region (3) and said fastening adhesive (50) has a width in transverse direction in the range of 45 mm to 110 mm at least at one point in said second region (2).

4. An article (20) according to claim 1 characterized in that said fastening adhesive (50) in said second region (2) is provided in a rectangular pattern relative to said centerlines (L, T).

5. An article (20) according to claim 1 characterized in that said article (20) further comprises wings (25) having an extension in longitudinal direction of at least 80% of the length of said first region (1) and extending at least within said first region (1), preferably not extending more than 20% of the length of said third region (3) into said third region (3) and more preferably not extending more than 15% of the length of said second region (2) into said second region (2).

6. An article (50) according to claim 1 which is a sanitary napkin.

* * * * *